United States Patent [19]
Parks

[11] 3,979,436
[45] Sept. 7, 1976

[54] OXIDATION RESISTANT POLYMERIC COMPOSITIONS
[75] Inventor: Carl R. Parks, Akron, Ohio
[73] Assignee: The Goodyear Tire & Rubber Company, Akron, Ohio
[22] Filed: Mar. 13, 1974
[21] Appl. No.: 450,696

Related U.S. Application Data
[62] Division of Ser. No. 153,446, June 15, 1971, Pat. No. 3,817,916.

[52] U.S. Cl. .......................................... 260/486 R
[51] Int. Cl.² ...................................... C07C 69/54
[58] Field of Search ............ 260/471 A, 471 R, 519, 260/571, 486 R

[56] References Cited
UNITED STATES PATENTS
3,843,710    11/1974    Buckler et al. ................. 260/471 A Primary Examiner—Paul J. Killos
Attorney, Agent, or Firm—F. W. Brunner; J. A. Rozmajzl

[57] ABSTRACT

Antioxidants such as the reaction product of p-aminodiphenylamine and glycidyl methacrylate [3-N-(4'-anilinophenyl)amino-2-hydroxypropyl methacrylate], and the reaction product of n-hexyl-N'-phenyl-p-phenylenediamine and glycidyl methacrylate [3-[N-(4'-anilinophenyl)-N-(1,3-dimethylbutyl)]amino-2-hydroxypropyl methacrylate], age resistant polymers having monomeric age resistors physically combined therewith and oxidation resistant polymeric compositions prepared by free radical polymerization techniques involving the use of said antioxidants as monomers.

6 Claims, No Drawings

OXIDATION RESISTANT POLYMERIC COMPOSITIONS

This is a division of Applicaton Ser. No. 153,446 filed June 15, 1971, and issued June 18, 1974, as U.S. Pat. No. 3,817,916.

This invention relates to monomeric antioxidants, oxidation resistant polymeric compositions and processes for preparing said monomeric antioxidants and oxidation resistant compositions. More particularly, the invention relates to a process of preparing polymeric compositions contaning antioxidants which are not susceptible to solvent extraction and which are resistant to volatilization.

Essentially all types of rubber, both natural and synthetic, and particularly rubbers formed from dienes, are known to be susceptible to deterioration resulting from prolonged exposure to oxidative aging. A great deal of effort has been expended by those engaged in the field of polymer technology to develop various stabilizers that will effectively inhibit the adverse effects of aging of polymeric compositions. Unfortunately, many of the commercially accepted stabilizers may be volatilized when the polymeric products are exposed to elevated temperatures and/or high vacuum over prolonged periods of time. Furthermore, they are rather quickly extracted from polymeric compositions by repeated washings with aqueous detergent solutions or organic solvents. These severe conditions are routinely encountered by garments containing latex treated fabric when they are subjected to frequent laundering or dry-cleaning.

It is, therefore, an object of this invention to provide a process for preparing oxidation resistant polymeric compositions. A further object of this invention is to provide a process of preparing polymeric compositions that are highly resistant to oxidative aging at elevated temperatures even after repeated exposure to aqueous detergent solutions or dry-cleaning fluids. It is still further object of this invention to provide a process of preparing polymers possessing antioxidants chemically bound thereto.

In accordance with the present invention oxidation resistant polymeric compositions are prepared by polymerizing a monomeric amine antioxidant with one or more comonomers.

The amine antioxidants of the present invention have the following structural formula.

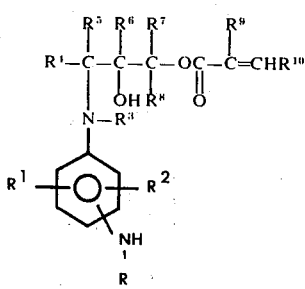

(I)

wherein R is selected from the group consisting of alkyl radicals having 1 to 12, preferably 3 to 12, carbon atoms, cycloalkyl radicals having 5 to 12 carbon atoms, aralkyl radicals having 7 to 24 carbon atoms and aryl radicals having 6 to 24 carbon atoms wherein $R^1$ and $R^2$ are selected from the group consisting of hydrogen and alkyl groups having 1 to 4 carbon atoms and wherein $R^3$ is selected from the group consisting of hydrogen, alkyl radicals having 1 to 12 (preferably 1 to 8) carbon atoms, cycloalkyl radicals having from 5 to 12 carbon atoms, and aralkyl radicals having 7 to 24 carbon atoms, preferably a benzyl or α-phenethyl radical wherein $R^4$, $R^5$, $R^6$, $R^7$, and $R^8$ are selected from the group consisting of hydrogen and alkyl radicals having from 1 to 4 carbon atoms, i.e. methyl, ethyl, propyl, and butyl radicals, the sum of the carbon atoms in $R^4$ and $R^5$ preferably being 4 or less, and the sum of carbon atoms in $R^7$ and $R^8$ preferably being 4 or less; wherein $R^9$ is selected from the group consisting of hydrogen; alkyl radicals having from 1 to 4 carbon atoms, i.e., methyl, ethyl, propyl, and butyl radicals; carboxymethyl radical and carbalkoxymethyl radicals; and wherein $R^{10}$ is selected from the group consisting of hydrogen; alkyl radicals having from 1 to 4 carbon atoms, i.e., methyl, ethyl, propyl, and butyl radicals; phenyl and substituted phenyl radicals, e.g., a phenyl group having located in the para position, an alkyl radical having 1 to 4 carbon atoms such as methyl, or an alkoxy radical having 1 or 2 carbon atoms, e.g., methoxy; carboxyl radical and carbalkoxy radicals.

Preferably —NH—R is in the para position.

Under structural formula (I), the carbalkoxymethyl radicals preferably have the following structural formula:

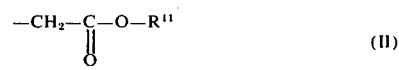

(II)

wherein $R^{11}$ is an alkyl radical having from 1 to 4 carbon atoms. The carbalkoxy radicals preferably have the following structural formula:

(III)

wherein $R^{12}$ is an alkyl radical having from 1 to 4 carbon atoms.

In structural formula (I), preferably $R^9$ is hydrogen or methyl. Preferably $R^{10}$ is hydrogen. In structural formula (II), $R^{11}$ is preferably methyl or ethyl. In structural formula (III), $R^{12}$ is preferably methyl or ethyl.

The amine age resisters of the present invention are illustrated by the following compounds.

3'-(4''-anilino anilino)-2'-hydroxypropyl methacrylate

3'-N-(4''-anilinophenyl)amino-2'-hydroxy-1'-methylpropyl methacrylate

3'-N-(4''-anilinophenyl)amino-2'-hydroxy-1', 2', 3'-trimethylpropyl methacrylate 3'-N-(4''-anilinophenyl)amino-2'-hydroxy-1', 1'-di-n-butylpropyl methacrylate 3'-N-(4''-anilinophenyl)amino-2'-hydroxypropyl acrylate 3'-N-(4''-anilinophenyl)amino-2'-hydroxypropyl-2-methoxy methacrylate 3'-N-(4''-anilinophenyl)amino-2'-hydroxypropyl-2-carboxy methacrylate 3'-N-(4''-anilinophenyl)amino-2'-hydroxypropyl-3-phenyl methacrylate
3'-N-(4''-anilinophenyl)amino-2'-hydroxypropyl-3-methoxy methacrylate
3'-N-(4''-anilinophenyl)amino-2'-hydroxypropyl-3-(4-carboxy phenyl) methacrylate
3'-N-(4''-anilinophenyl)amino-2'-hydroxypropyl-3-(4-carbmethoxy phenyl) methacrylate
3'-N-(4''-anilinophenyl)-N-isopropylamino-2'-hydroxypropyl methacrylate
3'-N-(4''-anilino-3''-methylphenyl)amino-2'-hydroxypropyl methacrylate
3'-N-(4''-anilino-3''-cyanoethylphenyl)amino-2'-hydroxypropyl methacrylate
3'-N-(4''-anilino-2''-tolylphenyl)amino-2'-hydroxypropyl methacrylate
3'-N-(4''-anilino-2''-cyclohexylphenyl)amino-2'-hydroxypropyl methacrylate
3'-N-(4''-anilino-2''-benzylphenyl)amino-2'-hydroxypropyl methacrylate
3'-N-[4''-(2''-methylanilino)phenyl]amino-2'-hydroxypropyl methacrylate
3'-N-[4''-(2''-cyanomethylanilino)phenyl]amino-2'-hydroxypropyl methacrylate
3'-N-[4''-(2''-tolylanilino)phenyl]amino-2'-hydroxypropyl methacrylate
3'-N-[4''-(4''-cyclohexylanilino)phenyl]amino-2'-hydroxypropyl methacrylate
3'-N-[4''-benzylanilino)phenyl]amino-2'-hydroxypropyl methacrylate When polymerized, the amine antioxidants of the present invention form segmers having the following structural formula.

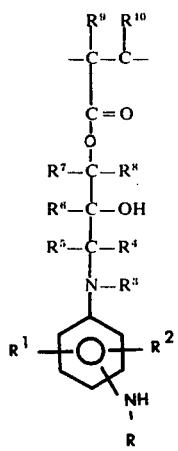

The monomeric antioxidants can easily be prepared by dissolving the aforementioned amines in a solvent such as benzene, adding a phenol or phenolate catalyst, such as sodium or potassium phenolate, and then slowly adding the epoxy compound. Preferably the reaction composition is heated and stirred for several hours, for example at 50°C. to 60°C. for 2 hours. The solvent is then removed, e.g., by a rotary evaporator.

The amine age resisters which are used within the practice of the present invention can be prepared by reacting (A) at least one amine compound as described hereinafter with at least one epoxy compound having the following structural formula:

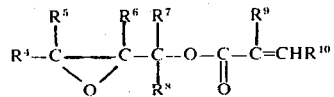

Representative epoxy compounds which can be used to prepare the monomeric age resisters of the present invention are:
 Glycidyl methacrylate
 Glycidyl-3-methyl methacrylate
 Glycidyl-3-phenyl methacrylate
 Glycidyl-3-n-butyl methacrylate
 Glycidyl-3-cyclohexyl methacrylate
 Glycidyl acrylate
 Glycidyl crotonate
 Glycidyl-3-n-butyl acrylate
 Glycidyl cinnamate
 Glycidyl-3-cyclohexyl acrylate
 Glycidyl-2-n-propyl acrylate
 Glycidyl-2-n-butyl acrylate The epoxy compounds can be prepared by the reaction of epichlorohydrin with a carboxylic acid in the presence of a base.

The amine compounds which can be reacted with the aforementioned epoxy compounds to prepare the amine age resisters of the present invention conform to the following structural formula.

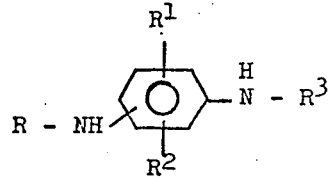

In preparing the amine antioxidants of the present invention, consideration should be given to the activities of the R—NH— and R³—NH— groups with epoxy groups. If one amine group is more reactive with epoxy groups than the other amine group, there is a greater possibility that the amine reactant will react with one, rather than two epoxy groups. The activity of the amine groups is dependent upon the nature of the R and R³ radicals. Normally amine groups possessing alkyl or aralkyl substituents are more reactive than amine groups containing aryl substituents. Amine groups possessing large substituents are generally less reactive with epoxy groups than amine groups containing smaller substituents.

Representative amine compounds which can be used to prepare the monomeric age resisters of the present invention are:
 N,N'-dimethyl-p-phenylenediamine
 N,N'-di-beta-naphthyl-p-phenylenediamine
 N,N'-bis(1-ethyl-3-methylpentyl)-p-phenylenediamine
 N,N'-bis(1-methylheptyl)-p-phenylenediamine
 N,N'-bis(sec.butyl)-p-phenylenediamine
 N-phenyl-N'-beta-hydroxyethyl-p-phenylenediamine
 N-phenyl-N'-cyanoethyl-p-phenylenediamine
 N-sec.butyl-N'-cyanoethyl-p-phenylenediamine
 N-beta-naphthyl-N'-sec.)butyl-p-phenylenediamine N,N'-diphenethyl-p-phenylenediamine
N-methyl-N'-phenyl-p-phenylenediamine
N-ethyl-N'-phenyl-p-phenylenediamine
N-isopropyl-N'-phenyl-p-phenylenediamine
N-sec.butyl-N'-phenyl-p-phenylenediamine
N-cyclohexyl-N'-phenyl-p-phenylenediamine
N-1,3-dimethylbutyl-N'-phenyl-p-phenylenediamine
N-1-methylheptyl-N'-phenyl-p-phenylenediamine
N-phenethyl-N'-phenyl-p-phenylenediamine
N-benzyl-N'-phenyl-p-phenylenediamine A particularly representative amine is p-aminodiphenylamine.

Para-aminodiphenylamine and the rest of the amine compounds which can be used to prepare the monomeric antioxidants of the present invention are known in the prior art and can be prepared by well known prior art methods. U.S. Pat. NO. 2,381,015; U.S. Pat. No. 3,209,030 and British Pat. No. 1,064,958 illustrate some prior art methods.

The aforementioned monomeric antioxidants may be polymerized by well known free radical polymerization techniques with one or more comonomers that are known to polymerize in free radical initiated polymerization systems. The polymerization may be carried out in emulsion, suspension, bulk or solution type systems. Some adjustments in the polymerization recipe and/or conditions may be necessary to obtain a satisfactory rate of polymer formation, depending on the amount of monomeric antioxidant included and the other monomers involved. Adjustments which may be necessary in the polymerization conditions to improve polymerization rates include increasing the temperature of polymerization and/or increasing the initiator level and/or increasing the level of activator ingredients. Solvents may also be required to obtain adequate solubility of the monomers with each other as well as to solubilize other ingredients where required. Some solvents, such as methyl ethyl ketone or isopropyl alcohol, can be used to advantage with an emulsion polymerization system. These adjustments, where necessary, are to counteract the inhibitory effect of the monomeric antioxidant and to insure its solubility in the system.

Examples of free initiators that are useful in the practice of this invention are those known as "Redox" initiators, such as appropriate combinations of chelated iron salts, sodium formaldehyde sulfoxylate and organic hydroperoxides such as cumene and paramenthane hydroperoxides. Other initiators such as azoisobutyronitrile, benzoyl peroxide, hydrogen peroxide and potassium persulfate may also be used, depending on the particular polymerization system.

The special monomers used in the practice of this invention have certain chemical characteristics which preclude their use in polymerization processes other than those initiated by free radicals. By "free radical initiated systems" is meant systems wherein free radicals are generated by any of various processes such as thermal decomposition of various persulfate, perborate, peroxide, azo or azonitrile compounds; induced (catalytic or "Redox" promoted) decomposition of various persulfate, peroxide or hydroperoxide compounds and generation of free radicals by exposure of the system to high energy radiation such as radiation from a radioactive source or ultraviolet light. Such systems are very well known in the art and are widely used commercially, e.g., in the preparation of SBR, styrene/butadiene copolymers.

The most widely used system for preparation of elastomeric polymers, i.e., polymers prepared from a monomer charge made up of at least 40 percent diene, preferably at least 60 percent diene, by free radical initiation is the emulsion system. Polymers ranging all the way from liquid, low molecular weight* (mol wts of about 1,000 to 5,000) to polymers of (molecular weight (60,000 to 70,000 and higher) to oil extendable, at least 50 percent soluble, rubbery solid, high molecular weight (100,000 to 500,000 or more) and even highly gelled, less than 50 percent soluble, may be prepared by emulsion polymerization. The monomeric age resisters of the present invention can be used in such emulsion polymerization systems to produce polymers of the aforementioned type.

*number average molecular weights

The principles of emulsion polymerization are discussed in references such as "Synthetic Rubber" by G. S. Whitby, Editor-in-Chief, John Wiley and Sons, 1954, particularly Chapter 8, and "Emulsion Polymerization" by F. A. Bovey et al, Vol IX of "High Polymers," Interscience Publishers Inc. 1955. Some specialized applications of these principles are indicated in U.S. Pat. Nos. such as 3,080,334; 3,222,334; 3,223,663; 3,468,833 and 3,099,650.

Very effective as free radical polymerization initiators used within the practice of the present invention, when used under appropriate conditions, are compounds such as t-butyl hydroperoxide and paramenthane hydroperoxides, and even hydrogen peroxide. These compounds perform very effectively when used in polymerization recipes containing appropriate levels of supporting ingredients. By "supporting ingredients" is meant those materials often referred to as activators in emulsion, or other systems, where required. U.S. Pat. No. 3,080,334 describes some of these materials at column 5, lines 20–26. Such materials can also be referred to as catalyst activators. The term "Redox Polymerization" is often used where the complete initiation system includes a Redox system, i.e., reducing agents and oxidizing agents in a proportion that yields polymerization initiating species. All of these initiator systems are well known in the art.

Emulsion and suspension polymerizations are normally accomplished in the range of 5°C. to 90°C. while the temperature range for solution or bulk polymerizations is normally 20°C. to 150°C. Though the activated or "Redox" initiated systems are preferred for low temperature polymerizations, they are very effective at high temperatures also, normally requiring appreciably lower quantities of the various ingredients to obtain a desirable polymerization rate.

The free radical sources used in the initiator systems are those customarily used in free radical polymerizations, for example, organic initiators such as azonitriles, azo-derivatives, peroxides, and hydroperoxides and inorganic initiators such as inorganic peroxy compounds. Radiation, e.g., of the ultra-violet and gamma type can also be used as a free radical source. Various organic initiators are described by J. Brankrup and E. H. Immergut, *Polymer Handbook* (John Wiley and Sons), 1965, pages II-3 to II-51. Peroxide initiators include the aralkyl, aliphatic, aliphatic acyl, aromatic acyl, ketone, aldehyde and perester types. Hydroperoxide compounds include aralkyl and aliphatic hydroperoxides. Inorganic peroxy compounds include persulfates, perborates, perphosphates and hydrogen peroxide.

Aralkyl peroxides are represented by dicumyl peroxide; aliphatic peroxides by di tert.butyl peroxide; aliphatic acyl peroxides by acetyl peroxide, decanoyl peroxide and lauroyl peroxide; aromatic acyl peroxides by benzoyl peroxide and 2,4-di-chlorobenzoyl peroxide; ketone peroxides by methylethyl ketone peroxide and cyclohexanone peroxide; aldehyde peroxides by heptaldehyde peroxide; and perester peroxides by tert.butyl peracetate, tert.butyl perpivalate and tert.butyl perbenzoate. Aralkyl hydroperoxides are represented by cumene hydroperoxide and diisopropylbenzene hydroperoxide and aliphatic hydroperoxides by tert.butyl hydroperoxide and paramenthane hydroperoxide. Persulfate, perborate and perphosphate compounds are represented by the sodium, potassium and ammonium persulfates, perborates and perphosphates; azo-nitriles and azo-derivatives by 2,2'-azo-bis-isobutyronitrile, 2,2'-azo-bis-2-methylpropionitrile and azo-bis-diphenylmethane.

Supporting ingredients, i.e., activators capable of activating certain initiators to produce free radicals include iron compounds such as ferrous sulfate or cobalt compounds, complexed with compounds such as sodium salts of ethylene diamine tetra acetic acid or sodium or potassium pyrophosphate. Reducing agents used in Redox systems include sodium formaldehydesulfoxylate, various sugars and hydrosulfites.

Various initiator system components are described column 4, lines 14 to ;b 32, in U.S. Pat. No. 3,080,334.

Examples of comonomers that are useful in the practice of this invention in combination with the monomeric antioxidants are polymerizable unsaturated hydrocarbons, both substituted and unsubstituted, including conjugated diene monomers, such as butadiene-1,3; 2-chlorobutadiene-1,3; isoprene; 2-ethyl-butadiene-1,3; piperylene; and hexadienes and copolymerizable monoolefins including vinyl and vinylidene monomers such as styrene, α-methylstyrene, divinyl benzene, vinyl chloride, vinyl acetate, vinylidene chloride, methylmethacrylate, ethylacrylate, the vinylpyridines including 2-vinyl pyridine, 5-methyl-2-vinylpyridine, 4-vinyl pyridine and 2-vinyl-5-ethyl pyridine, acrylonitrile, methacrylonitrile, methacrylic acid and acrylic acid. Mixtures of the monomeric antioxidants and mixtures of the comonomers may be used. The monomer charge weight ratio is normally from about 0.10/99.9 to about 10/90 or even 20/80 monomeric antioxidant-/comonomer. The ratio may even be as high as 30/70 or 60/40. A charge ratio of about 0.5/99.5 to about 5.0/95 is preferred. Ratios will vary depending on the amount of antioxidant desired to be bound and on the reactivity ratios of the monomers in the particular polymerization system used. However, the ratio may be even higher and the monomeric antioxidant may even constitute all of the monomer charged, i.e., the ratio can be 100/0.

Preferably the monomer system contains at least 50 parts by weight per 100 parts by weight of total monomer of at least one diene, preferably a conjugated diene, such as 1,3-butadiene or isoprene. It always contains at least 40 parts by weight of said diene.

One embodiment of the present invention involves the use of a monomer system comprised of from about 50 to about 99.9 parts of at least one diene monomer, preferably a conjugated diene, 0 to about 49.9 parts of at least one monomer selected from the group consisting of vinyl monomers and vinylidene monomers and from about 0.10 to 5.0 parts by weight of at least one monomeric antioxidant, all parts being parts by weight per 100 parts by weight of total monomer. Preferably at least 0.5 part of monomeric antioxidant is used. When at least 0.5 part of the monomeric antioxidant is used, the upper limit on the diene monomer range is 99.5 parts and the upper limit of the vinyl monomer and/or vinylidene monomer range is 49.5 parts. The upper limit of the monomeric antioxidant range may be even higher than 5.0, i.e., 10, 20, 30 and even 50.

The polymers resulting from the free radical polymerizations of monomeric systems containing the monomeric antioxidants of the present invention have a special advantage in that the age resistant portion is not extractable, and therefore the polymeric compositions are highly resistant to oxidative aging even after repeated exposure to aqueous detergent solutions or dry-cleaning fluids. This feature is especially significant where polymers are used in foam backings for rugs and where polymers are used in solution or latex form to treat fabrics, since such products are often exposed to aqueous detergent solutions or dry-cleaning fluids. This feature is also significant where factors such as contact with lubricating oils or exposure to high vacuum conditions are a consideration.

One of the advantages of the present process is that it permits the preparation of polymers prepared from monomer systems containing diene monomers and containing built-in-stabilizers, without the formation of appreciable gel, that is, polymers can be made which are essentially gel-free. Gel formation is generally undesirable in a polymer since it can cause processing difficulties and directly and/or indirectly can affect affect physical properties of the polymer in its vulcanized form. Normally a macro gel content of less than 50 percent is desirable. Preferably a gel content of less than 10 percent is desirable. Most preferably a gel content below 5 percent is desirable. Gel is the amount of polymer that is insoluble in an organic solvent such as benzene. One way to measure gel content comprises placing about 0.20 to about 0.30 grams of the polymer in 100 milliliters of benzene and permitting the mixture to stand for 48 hours. The mixture is then filtered through a 100 mesh stainless steel wire cloth having a wire diameter of 0.045 inch. A solids is then run on the filtrate to determine the amount of soluble polymer. The amount of gel is the difference between the amount of polymer placed in the benzene originally and the amount of soluble polymer. The percent gel is one hundred times the gel weight divided by the original polymer weight.

To afford adequate protection against degradation the polymers should contain from about 0.10 part to about 10.0 parts by weight of the segmeric form of the monomeric antioxidant per 100 parts by weight of the polymer, although from about 0.50 part to about 5.0 parts is normally satisfactory, from about 0.50 part to about 3.0 parts being preferred. As much as 20 parts, 30 parts, 50 parts and more of the polymer may consist of the antioxidant segmeric unit while the lower limit may be 0.50 part to 0.10 part and lower. In fact, polymers containing 100 percent antioxidant segmeric units may be produced, if desired. However, as the amount of bound antioxidant increases the physical characteristics of the polymer are altered accordingly. Where it is desired to produce a polymer which is self stabilizing and which substantially retains the physical properties of the comonomer or comonomers, normally the polymer should contain no more than about 10.0 parts by weight of the antioxidant segmeric unit, i.e., repeat unit. Such polymers preferably are solid, although they may be liquid. Where it is desired that the polymer act as a polymeric antioxidant which may be blended with unstabilized polymers the polymer should normally contain greater amounts of the monomeric antioxidant. The remainder of the polymer is comprised preferably of the segmeric form of at least one conjugated diene monomer and/or the segmeric form of at least one vinyl monomer. Preferably the polymers contain at least 50 percent by weight of the segmeric form of a diene, preferably a conjugated diene such as butadiene-1,3 or isoprene. Most preferred are polymers containing from about 50 to about 99.9 parts by weight of the segmeric form of at least one diene, preferably a conjugated diene, 0 to about 49.9 parts by weight of the segmeric form of at least one monomer selected from the group consisting of vinyl monomers and vinylidene monomers and 0.10 to 5.0 parts by weight of the segmeric form of at least one monomeric antioxidant, all parts being by weight per 100 parts by weight of polymer. Preferably the polymer contains at least 0.5 part of the segmeric form of the monomeric antioxidant. When the polymer contains at least 0.5 part of the segmeric form of the monomeric antioxidant, the upper limit of diene segmer range is 99.5 parts and the upper limit of the vinyl segmer and/or vinylidene segmer range is 49.5 parts. The upper limit of the segmeric form of the monomeric antioxidant range may be even higher than 5.0, i.e., 10, 20, 30 and even 50. In all instances the polymers must contain at least 40 parts by weight of the segmeric form of a diene monomer, preferably a conjugated diene. In polymers generally prepared by free radical, particularly emulsion techniques, the trans-1,4 content is generally greater than the cis-1,4 or 1,2 content.

All of the monomeric amine antioxidants described herein are capable of stabilizing polymers by simple incorporation into the polymers by conventional techniques such as by addition to polymer latices or by addition to the solid polymer on a mill or in a Banbury. When blending a self-stabilizing polymer with other polymers, especially when the self-stabilizing polymer contains large amounts of the segmeric form of the monomeric antioxidant, one must consider the solubility problems involved in blending dissimilar polymers.

Polymers subject to deterioration by oxidation that can be conveniently protected by the antioxidants described herein include substituted and unsubstituted, saturated and unsaturated, natural and synthetic polymers. The oxidizable natural polymers include rubber in its various forms, e.g., pale crepe and smoked sheet, and balata and gutta percha. The oxidizable synthetic polymers are prepared from a single monomer (homopolymer) or a mixture of two or more copolymerizable monomers (copolymers) wherein the monomers are combined in a random distribution or block form. The monomers may be substituted or unsubstituted and may possess one or more double bonds, for example, diene monomers, both conjugated and nonconjugated, and monoolefins including cyclic and acyclic monoolefins, especially vinyl and vinylidene monomers. Examples of conjugated dienes are 1,3-butadiene, isoprene, chloroprene, 2-ethyl-1,3-butadiene, 2,3-dimethyl-1,3-butadiene and piperylene. Examples of nonconjugated dienes are 1,4-pentadiene, 1,4-hexadiene, 1,5-hexadiene, dicyclopentadiene, 1,5-cyclooctadiene and ethylidene norbornene. Examples of acyclic monoolefins are ethylene, propylene, 1-butene, isobutylene, 1-pentene and 1-hexene. Examples of cyclic monoolefins are cyclopentene, cyclohexene, cycloheptene, cyclooctene and 4-methyl-cyclooctene. Examples of vinyl monomers are styrene, acrylonitrile, acrylic acid, ethylacrylate, butylacrylate, methyl vinyl ether, vinyl acetate and vinyl pyridine. Examples of vinylidene monomers are α-methylstyrene, methacrylic acid, methyl methacrylate, ethyl methacrylate, glycidyl methacrylate and vinylidene chloride. Representative examples of the synthetic polymers used in the practice of this invention are polychloroprene; homopolymers of a conjugated 1,3-diene such as isoprene and butadiene, and in particular, polyisoprenes and polybutadienes having essentially all of their repeat units combined in a cis-1,4 structure; copolymers of a conjugated 1,3-diene such as isoprene and butadiene with up to 50 percent by weight of at least one copolymerizable monomer including ethylenically unsaturated monomers such as styrene or acrylonitrile; butyl rubber, which is a polymerization product of a major proportion of a monoolefin and a minor proportion of a multiolefin such as butadiene or isoprene; polyurethanes containing carbon to carbon double bonds; and polymers and copolymers of monoolefins containing little or no unsaturation, such as polyethylene, polypropylene, ethylene propylene copolymers and terpolymers of ethylene, propylene and a nonconjugated diene such as dicyclopentadiene, 1,4-hexadiene, ethylidene norbornene and methylene norbornene.

When added in free form normally 0.001 to 10.0 percent of the antioxidant by weight, i.e., parts by weight based on the weight of the polymer, i.e., 100 parts by weight of the polymer can be used, although the precise amount of the antioxidant which is to be employed will depend somewhat on the nature of the polymer and the severity of the deteriorating conditions to which the polymer is to be exposed. In unsaturated polymers such as those made from conjugated dienes, the amount of antioxidant necessary is greater than that required by a saturated polymer such as polyethylene. It has been found that an effective antioxidant amount of the disclosed stabilizers in rubbery unsaturated polymers will generally range from 0.05 to 5.0 percent by weight i.e., parts by weight based on the weight of the polymer, although it is commonly preferred to use from 0.5 to 3.0 percent by weight, i.e., parts by weight based on the weight of the polymer. Mixtures of the antioxidants may be used.

The following examples illustrate the practice of the present invention. Unless otherwise indicated, all parts are parts by weight.

EXAMPLE 1

Para-aminodiphenylamine (62.5 grams/0.34 mole) was dissolved in 670 ml. of benzene. The catalyst was prepared by adding one gram of sodium hydroxide and one gram of phenol to 5 ml. of water. Five milliliters of ethanol was added to insure solubility in the benzene. After adding the catalyst, 24 grams (0.169 mole) of glycidyl methacrylate was added slowly from a dropping funnel and the mixture was stirred for 18 hours at room temperature. The solvent was then removed with a rotary evaporator. The yield was 55 grams (93%). The melting point of the product was 126° C.

EXAMPLE 2

Ninety-one grams (0.34 mole) of N-1,3-dimethylbutyl-N'-phenyl-phenylenediamine were dissolved in 670 milliliters of benzene. Catalyst was prepared and glycidyl methacrylate was added as described above. The yield was 58 grams (84%).

Examples 1 and 2 were run using a 2/1 molar ratio of amine to methacrylate. A 1/1 molar ratio can be used to produce essentially the same products.

The following examples illustrate the preparation of polymers containing monomeric antioxidants as part of the polymeric chain. They also illustrate the oxidation resistance possessed by said polymers. Unless otherwise indicated all parts are parts by weight.

EXAMPLES 3 to 7

The following polymerizations were carried out using the following recipes.

nent was 3-[N-(4'-anilinophenyl)-N-(1,3-dimethylbutyl)]amino-2-hydroxypropyl methacrylate. The polymer of Example 19 was alcohol coagulated at 24 percent conversion. Each of the polymerizations was run for 22 hours.

Table IV

| Order of Addition | Ingredients | Parts |
|---|---|---|
| 1 | Water | 180 |
|  | Linear dodecyl benzene sulfonate | 5 |
|  | Sodium salt of condensed naphthalene sulfonic acid | .13 |
|  | Tripotassium phosphate | 0.40 |
| 2 | Acrylonitrile | 33 |
| 3 | t-dodecyl mercaptan | 0.33 |
| 4 | Monomeric antioxidant | 5 |
| 5 | Butadiene-1,3 | 67 |

Table III

| Order of Addition | Ingredients | Examples (parts) 12 | 13 | 14 | 15 | 16 |
|---|---|---|---|---|---|---|
| 1 | Water | 194 | 200 | 194 | 195 | 195 |
|  | Potassium soap of disproportionated rosin acids | 2.8 | 2.7 | 2.7 | 2.7 | 2.7 |
|  | Sodium soap of tallow fatty acids | 2.4 | 2.4 | 2.4 | 2.4 | 2.4 |
|  | Trisodium phosphate | — | .375 | .04 | .375 | .375 |
|  | Sodium hydrosulfite | — | — | — | .011 | .009 |
|  | Sodium salt of condensed naphthalene sulfonic acid | .08 | .08 | .15 | .08 | .08 |
|  | Tripotassium phosphate | .25 | — | — | — | — |
| 2 | Styrene | 20 | — | 20 | 20 | 20 |
|  | Acrylonitrile | — | 30 | — | — | — |
|  | Tertiary dodecyl mercaptan | .25 | .60 | .30 | .40 | .30 |
| 3 | Monomeric antioxidant(1) | 1.25 | 1.25 | 5.0 | 1.25 | 1.25 |
|  | Methyl ethyl ketone | 55 | 55 | — | 55 | 44 |
|  | Cyclohexanone | — | — | 45 | — | — |
| 4 | Butadiene-1,3 | 75 | 67 | 75 | 75 | 75 |
|  | Water | 5 | 11 | 5 | 11 | 11 |
|  | Chelating agent(2) | .077 | .038 | .077 | .038 | .023 |
| 5 | Ferrous sulfate heptahydrate | .02 | .0075 | .02 | .009 | .02 |
|  | Sodium formaldehyde sulfoxylate | .04 | .10 | .02 | .08 | .05 |
|  | Sodium hydrosulfite | .01 | .006 | .01 | .002 | .004 |
| 6 | Styrene | 2.4 | — | 2.4 | 2.4 | 2.4 |
|  | Acrylonitrile | — | 2.4 | — | — | — |
|  | Paramenthane hydroperoxide | .04 | .05 | .02 | .02 | .01 |
| Polymerization temperature (°F.) | | 41 | 77 | 45 | 70 | 122 |
| Polymerization time (hours) | | 13 | 19 | 10 | 10 | 12 |
| Percent conversion | | 65 | 79 | 65 | 66 | 60 |

(1)Approximately 1/1 (molar ratio) reaction product of glycidyl methacrylate and p-aminodiphenylamine, the major component being 3-N-(4'-anilinophenyl)amino-2-hydroxypropyl methacrylate. The antioxidant was dissolved in 3.54 parts of methyl ethyl ketone before being added to the system.
(2)90/10 mixture of tetrasodium salt of ethylene diamine tetraacetic acid and monosodium salt of N,N-di(α-hydroxyethyl) glycine.

The above polymerization systems were shortstopped with 0.10 part of sodium dimethyldithiocarbamate and 0.05 part of diethylhydroxylamine in 4.4 parts of water. A very small amount of sulfuric acid was added to at least one number 5 solutions to dissolve any ferrous hydroxide formed.

EXAMPLES 17, 18 and 19

The following recipe (Table IV) was used to prepare three polymers at 5° C. In Example 17 a 1/1 (molar ratio) reaction product of glycidyl methacrylate and p-aminodiphenylamine was used as the monomeric antioxidant. In Example 18 a 2/1 (molar ratio) was used. The major component in each was 3-N-(4'-anilinophenyl)amino-2-hydroxypropyl methacrylate. The polymerization systems were alcohol coagulated, Example 17 at 38.5 percent conversion and Example 18 at 10.0 percent conversion. In Example 19 the monomeric antioxidant was a reaction product (2/1 molar ratio) of glycidyl methacrylate and N-phenyl-N'-1,3-dimethylbutyl-p-phenylenediamine. The major compo-

| | | |
|---|---|---|
| 6 | Water | 17 |
|  | Chelating agent(2) | .075 |
|  | Sodium formaldehyde sulfoxylate | .022 |
|  | FeSO$_4$.7H$_2$O | .022 |
| 7 | Cumene hydroperoxide | .056 |
|  | Benzene | 2.4 |

Table V contains oxygen absorption data for the polymers prepared in Examples 12 to 19.

Before oxygen absorption tests were run on the polymers described in Table V, the dry polymers were extracted for 48 hours with methanol* in a Soxhlet type apparatus to remove any of the free monomeric age resister and dried. The amount of oxygen absorbed in a particular interval of time was determined for each sample and is listed in the following Table III. An unstabilized NBR rubber would absorb 1 percent O$_2$ at 100° C. in less than 10 hours.

*The SBR types were extracted with acetone.

Table III

| Example | Oxygen Absorption Hours to 1% O₂ at 100°C. | |
| --- | --- | --- |
| 3 | 293 and 345 | |
| 4 | 385 | (to .88% O₂) |
| 5 | 264 | |
| 6 | 418 | |
| 7 | 393 | |
| 8 | 410 | |
| 9 | 485 | |
| 10 | 410 | |

The above data demonstrate that the monomeric antioxidants described herein are capable of providing age resistant polymeric compositions by either polymerizing the monomeric antioxidants in an emulsion-free radical polymerization system along with comonomers. That is, the age resisters provide protection whether in a free or bound condition. Any of the monomeric antioxidants or polymers described earlier herein can be substituted for their counterparts in the above working examples to provide age resistant polymeric compositions.

NBR and SBR polymers were stabilized by physical incorporation of 1.47 and 1.25 parts respectively of a reaction product of glycidyl methacrylate and p-aminodiphenylamine (1/1 molar ratio). Both polymers were stabilized quite effectively.

Naturally polymerization rates and amounts of bound monomer can vary, as well as the type of emulsifier to be used, depending upon the monomers used. Also, reactor size and degree of agitation can affect polymerization rates. However, optimum conditions and systems can be determined based upon the above revelations by routine experimentation by one possessing ordinary skill in the art. Polymerization rates can often be improved by using a purified monomeric age resister and/or by raising the polymerization temperature, using more potent initiator systems, increasing the initiator level or by any of the conventional means of improving polymerization rates.

All polymer molecular weights referred to herein, unless otherwise indicated, are number average molecular weights.

The age resistant polymeric compositions prepared by chemically binding the antioxidants or by physically incorporating them into polymers, are age resistant, whether in vulcanized or unvulcanized form. They may be used, depending on the particular polymer involved, in products such as tires, industrial rubber products, such as transmission belts and hose, and molded goods. Where the polymeric composition contains the antioxidant as an integral part of the polymer chain, it is especially useful in applications where a product is frequently exposed to aqueous detergent solutions or dry-cleaning fluids, for example, in foam backings for rugs and in polymer treated fabrics.

While certain representative embodiments and details have been shown for the purpose of illustrating the invention, it will be apparent to those skilled in this art that various changes and modifications may be made therein without departing from the spirit or scope of the invention.

What is claimed is:

1. A composition of matter comprised of at least one compound selected from the group consisting of compounds having the following structural formula:

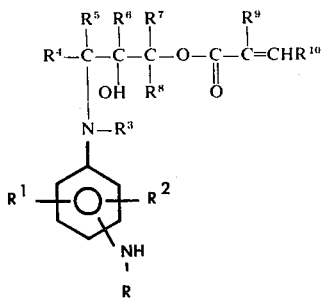

wherein R is selected from the group consisting of alkyl radicals having 1 to 12 carbon atoms, cycloalkyl radicals having 5 to 12 carbon atoms, aralkyl radicals having 7 to 24 carbon atoms and aryl radicals having 6 to 24 carbon atoms wherein $R^1$ and $R^2$ are selected from the group consisting of hydrogen and alkyl groups having 1 to 4 carbon atoms and wherein $R^3$ is selected from the group consisting of hydrogen, alkyl radicals having 1 to 12 carbon atoms, cycloalkyl radicals having from 5 to 12 carbon atoms, and aralkyl radicals having 7 to 24 carbon atoms, wherein $R^4$, $R^5$, $R^6$, $R^7$ and $R^8$ are selected from the group consisting of hydrogen and alkyl radicals having from 1 to 4 carbon atoms, and wherein $R^9$ and $R^{10}$ are selected from the group consisting of hydrogen and alkyl radicals having from 1 to 4 carbon atoms.

2. The composition according to claim 1 wherein -NH-R is in the para position.

3. The composition according to claim 1 wherein the sum of the carbon atoms in $R^4$ and $R^5$ are 4 or less and wherein the sum of carbon atoms in $R^7$ and $R^8$ are 4 or less.

4. The composition according to claim 1 wherein $R^8$ is selected from the group consisting of hydrogen and methyl and $R^9$ is hydrogen.

5. The composition according to claim 1 wherein $R^{11}$ and $R^{12}$ are selected from the group consisting of methyl and ethyl radicals.

6. The composition according to claim 1 wherein the composition is 3-N-(4'-anilinophenyl)amino-2-hydroxypropyl methacrylate.

* * * * *